US 6,564,098 B1

(12) United States Patent
Kerver (10) Patent No.: US 6,564,098 B1
(45) Date of Patent: May 13, 2003

(54) METHOD AND SYSTEM FOR INCREASING A PACER FUNCTION OF AN IMPLANTABLE MEDICAL DEVICE DISPOSED WITHIN A MAMMALIAN HEART

(75) Inventor: Harry B. A. Kerver, Duiven (NL)

(73) Assignee: Medtronic, Inc., Minneapolis, MN (US)

( * ) Notice: Subject to any disclaimer, the term of this patent is extended or adjusted under 35 U.S.C. 154(b) by 158 days.

(21) Appl. No.: 09/705,804

(22) Filed: Nov. 6, 2000

(51) Int. Cl.⁷ ............................................. A61N 1/365
(52) U.S. Cl. ...................................... 607/17; 607/30
(58) Field of Search .......................... 607/9, 10, 17, 607/18, 19, 21, 23, 25, 30; 600/485, 486

(56) References Cited

U.S. PATENT DOCUMENTS

| | | | | |
|---|---|---|---|---|
| 4,566,063 A | * | 1/1986 | Zolnowsky et al. | 711/125 |
| 4,899,751 A | * | 2/1990 | Cohen | 600/485 |
| 4,899,752 A | * | 2/1990 | Cohen | 600/485 |
| 5,101,824 A | * | 4/1992 | Lekholm | 607/18 |
| 5,144,949 A | * | 9/1992 | Olson | 607/17 |
| 5,158,078 A | * | 10/1992 | Bennett et al. | 607/27 |
| 5,271,395 A | * | 12/1993 | Wahlstrand et al. | 607/9 |
| 5,300,092 A | * | 4/1994 | Schaldach | 607/18 |
| 5,312,453 A | * | 5/1994 | Shelton et al. | 607/19 |
| 5,423,869 A | * | 6/1995 | Poore et al. | 607/18 |
| 5,447,523 A | * | 9/1995 | Schaldach | 607/19 |
| 5,824,019 A | * | 10/1998 | Rueter et al. | 607/17 |
| 5,944,743 A | | 8/1999 | Janssens | |
| 6,058,328 A | * | 5/2000 | Levine et al. | 607/14 |

OTHER PUBLICATIONS

P–4912 (V–0505) Letter titled "Pacemaker with Programmable Rate Variation for Treatment of Patients Following Ablation of the Atrio–Ventricular Junction"; (Author Hervé-Janssens; Dated May 21, 1996, 2 pp.).
Article titled "Bradycardia Dependent QT Prolongation and Ventricular Fibrillation Following Catheter Ablation of the Atrioventricular Junction with Radiofrequency Energy"; (Author Peters et al.; Dated Jun. 1994; Pace, vol. 17, pp. 108–112).
Abstract #65 titled "New Observations on the Problem of Ventricular Fibrillation and Sudden Death after Radiofrequency Ablation of the Atrioventricular Junction"; (Author Geelen et al.; Dated Apr. 1996; Pace, vol. 19, p. 582).
P–4517 Memo titled "Time Adaptive AVD"; (Author Chester Struble and Henri Heynen; Dated Jan. 17, 1996; 2 pp.).

* cited by examiner

Primary Examiner—Willis R. Wolfe
(74) Attorney, Agent, or Firm—Thomas F. Woods; Eric R. Waldkoetter; Tom G. Berry (57) ABSTRACT

A method and system for increasing a pacer function of an implantable medical device disposed within a mammalian heart is provided. Generally speaking, the present invention provides pacing the mammalian heart according to a first pacing rate. A command to increase the first pacing rate is then received. Additionally, an upper pacing rate is received. A time interval is then received. Finally, the first pacing rate of the mammalian heart is increased to the second pacing rate during the time interval.

48 Claims, 6 Drawing Sheets

METHOD AND SYSTEM FOR INCREASING A PACER FUNCTION OF AN IMPLANTABLE MEDICAL DEVICE DISPOSED WITHIN A MAMMALIAN HEART

FIELD OF THE INVENTION

The present invention relates to cardial pacing systems and methods, and, more particularly, to cardial pacing systems which provide for a method for increasing a pacer function of an implantable medical device disposed within a mammalian heart.

BACKGROUND OF THE INVENTION

Pacemaker systems with rate control have become widely used in the art. Rate control may be provided by employing one or more rate responsive sensors, e.g., sensors which determine a parameter such as a Q-T interval, exercise, etc., from which the desired pacing rate to match the patient's cardiac's demand can be determined. Such rate responsive pacemakers preferably contain algorithms for converting the sensed parameters into a pacing rate, e.g., increased activity results in a higher pacing rate. Furthermore, it is known to program certain data relating to pacing rate from an external programmer, e.g., the values of lower rate limit and upper rate limit may be programmed in this manner.

It has been determined that under special circumstances, it is desired to control the pacing rate of an implanted pacemaker in accordance with a special function. That is, a rate or rates which would not otherwise be indicated. For example, it has been determined that in some cases, an increase in the pacing rate of the heart may be required. Furthermore, it is a belief that an immediate increase in the pacing rate of the heart may be problematic for some patients. As a result, the pacing rate of the heart must necessarily be increased in an incremental manner (i.e. a "gentle" way of increasing the pacer function).

In Janssens, U.S. Pat. No. 5,944,743, there is disclosed a pacemaker system for enabling special rate control for patients who have specially recognized conditions, e.g. patients who are post-ablation and are best susceptible to bradycardia-dependent ventricular fibrillation or other arrhythmias. However, the disclosure in Janssens does not discuss the increase of a pacer function; rather, it discusses the decrease of a pacer function with regards to a specially recognized condition.

As discussed above, the most pertinent prior art patent is shown in the following table:

TABLE 1

Prior Art Patent.

| Patent No. | Date | Inventor(s) |
|---|---|---|
| 5,944,743 | Aug. 31, 1999 | Janssens et al. |

The patent listed in Table 1 is hereby incorporated by reference herein in its entirety. As those of ordinary skill in the art will appreciate readily upon reading the Summary of the Invention, the Detailed Description of the Preferred Embodiments and the Claims set forth below, many of the devices and methods disclosed in the patent of Table 1 may be modified advantageously by using the teachings of the present invention.

SUMMARY OF THE INVENTION

The present invention is therefore directed to providing a method and system for gently increasing the pacing function of a mammalian heart by an implantable medical device. Such a system of the present invention overcomes the problems, disadvantages and limitations of the prior art described above, and provides a more efficient and accurate means of increasing the pacing function of a mammalian heart.

The present invention has certain objects. That is, various embodiments of the present invention provide solutions to one or more problems existing in the prior art respecting the increment of the pace of a mammalian heart. Those problems include, without limitation: the ability to determine when a mammalian heart is required to have a pacing function increased, the ability to increase the heart rate of a mammalian heart, and the ability to increase the heart rate at a programmed rate.

In comparison to known techniques for increasing the pace of a mammalian heart, various embodiments of the present invention may provide the following advantage, inter alia, i.e., inputting an upper pacing limit, inputting an increment factor, inputting a time interval, and increasing the pacing function of a mammalian heart from a lower pacing limit to an upper pacing limit within the time period programmed and according to the increment factor.

Some of the embodiments of the present invention include one or more of the following features: an implantable medical device including a microprocessor, a controller operably connected to the microprocessor and at least one pacing lead operably connected to the controller.

Furthermore, in accordance with the present invention, a method and system for increasing a pacer function of an implantable medical device disposed within a mammalian heart is provided. Generally speaking, the present invention provides pacing the mammalian heart according to a first pacing rate. A command to increase the first pacing rate is then received. Additionally, an upper pacing rate is received. A time interval is then received. Finally, the first pacing rate of the mammalian heart is increased to the second pacing rate during the time interval.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

Figure 1:
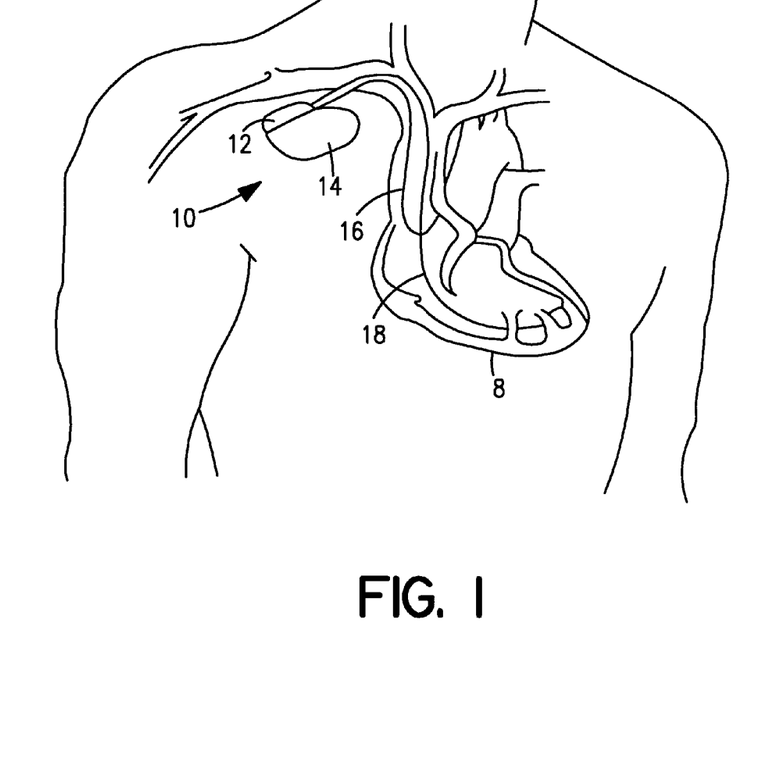
FIG. 1 is a schematic view of an embodiment of an implantable medical device, made in accordance with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
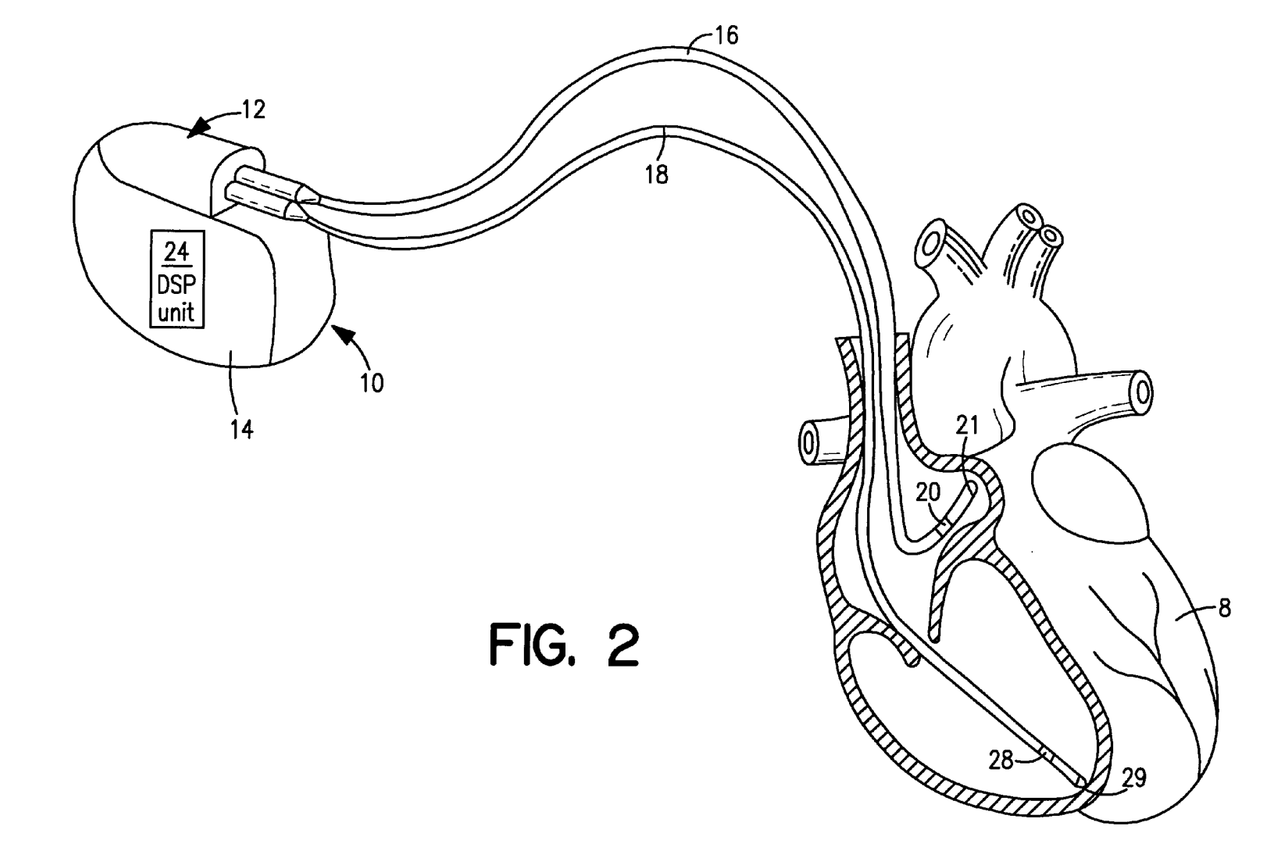
FIG. 2 is another view of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
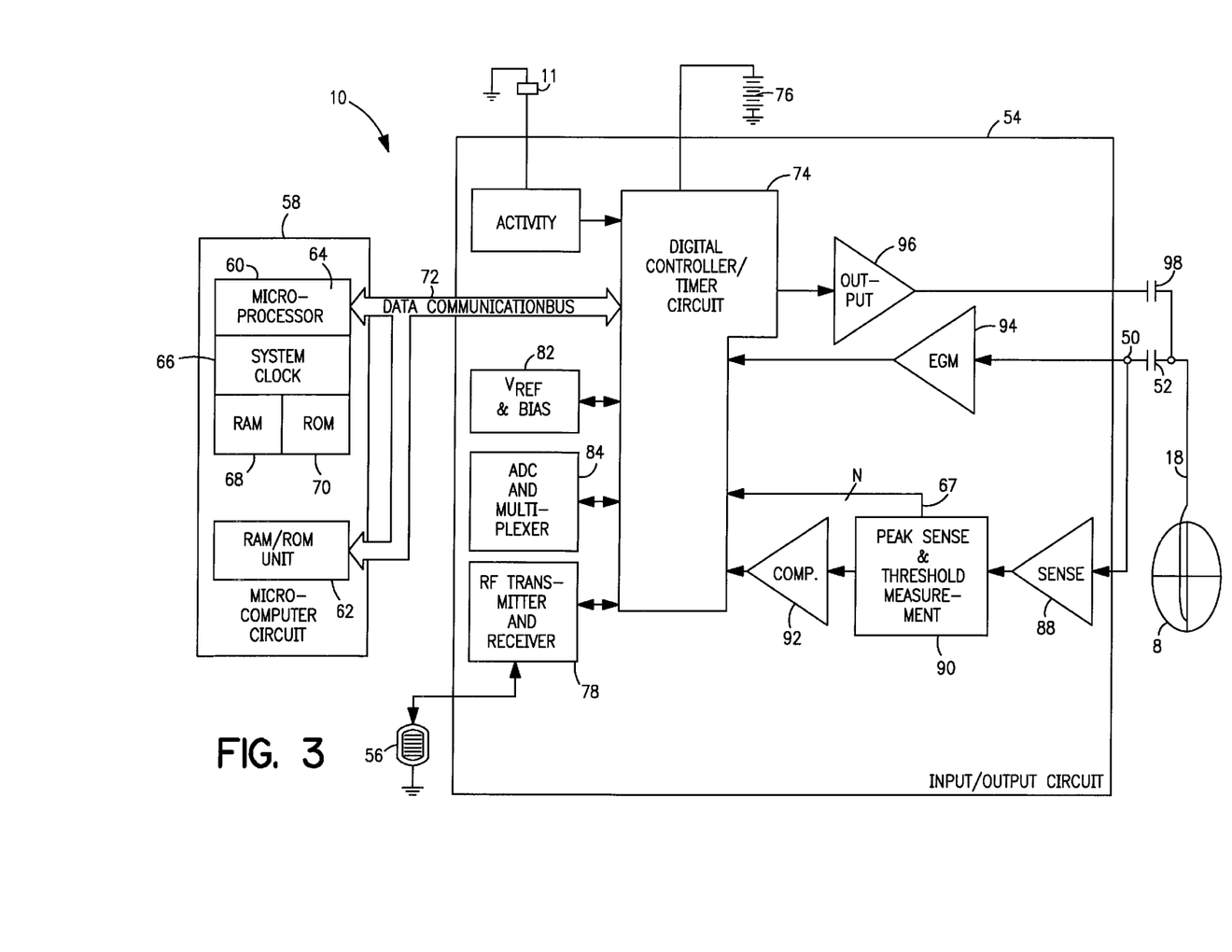
FIG. 3 shows a block diagram illustrating the components of the implantable medical device of FIG. 1, made in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al's '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, WI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter- defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
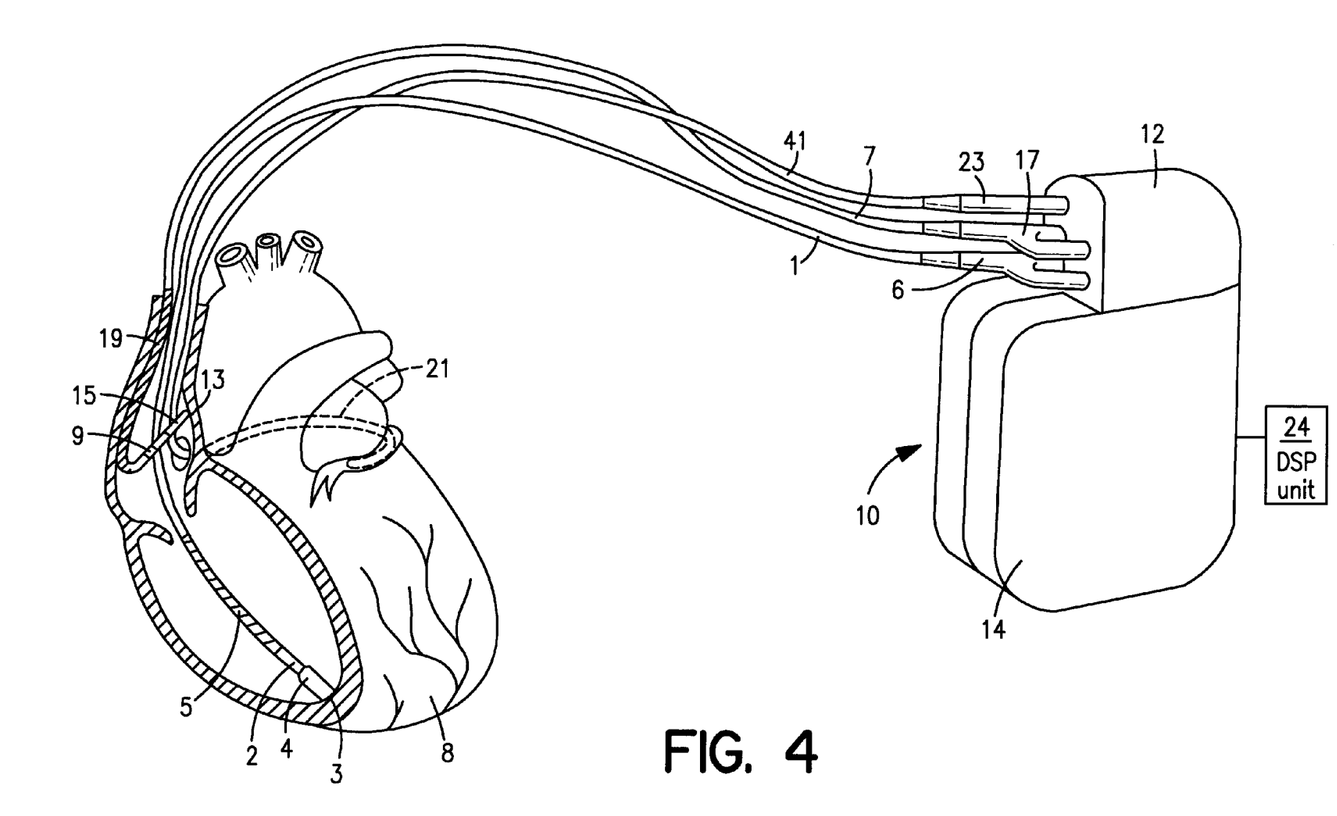
FIG. 4 illustrates another embodiment of an implantable medical device, made in accordance with the present invention.
Figure 5:
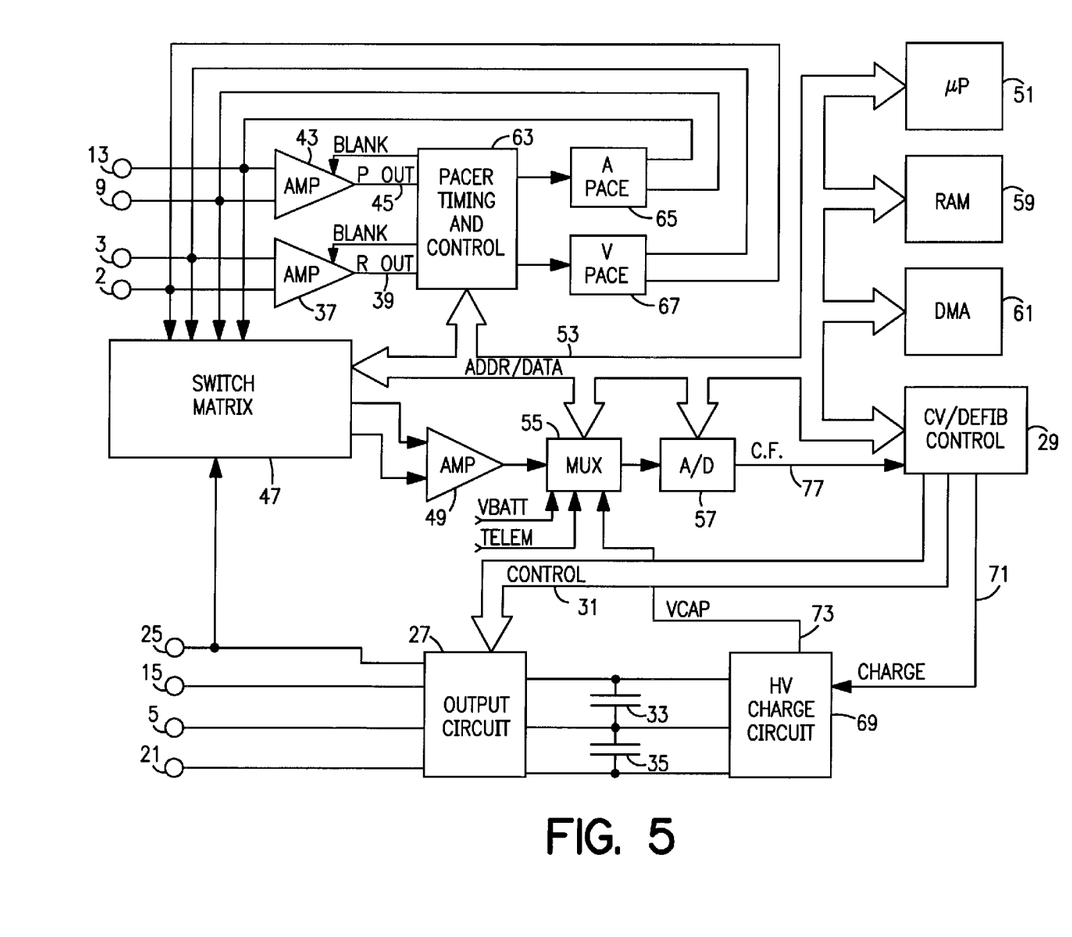
FIG. 5 illustrates a block diagram of the embodiment of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by OCV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of antitachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Winstrom, which is incorporated by reference herein, in its entirety, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are incorporated by reference herein, each in their respective entireties. The present invention is believed to find wide application to any form of implantable electrical device for use in conjunction with electrical leads.

The present invention comprises a method and system for increasing a pacer function of IMD 10 disposed within mammalian heart 8. Generally peaking, the present invention provides a method for pacing mammalian heart 8 according to a first pacing parameter. A command to increase the first pacing parameter is received. A second pacing parameter is received. A time interval is then received. Finally, the first pacing parameter of mammalian heart 8 is increased to the second pacing parameter during the time interval.

Figure 6:
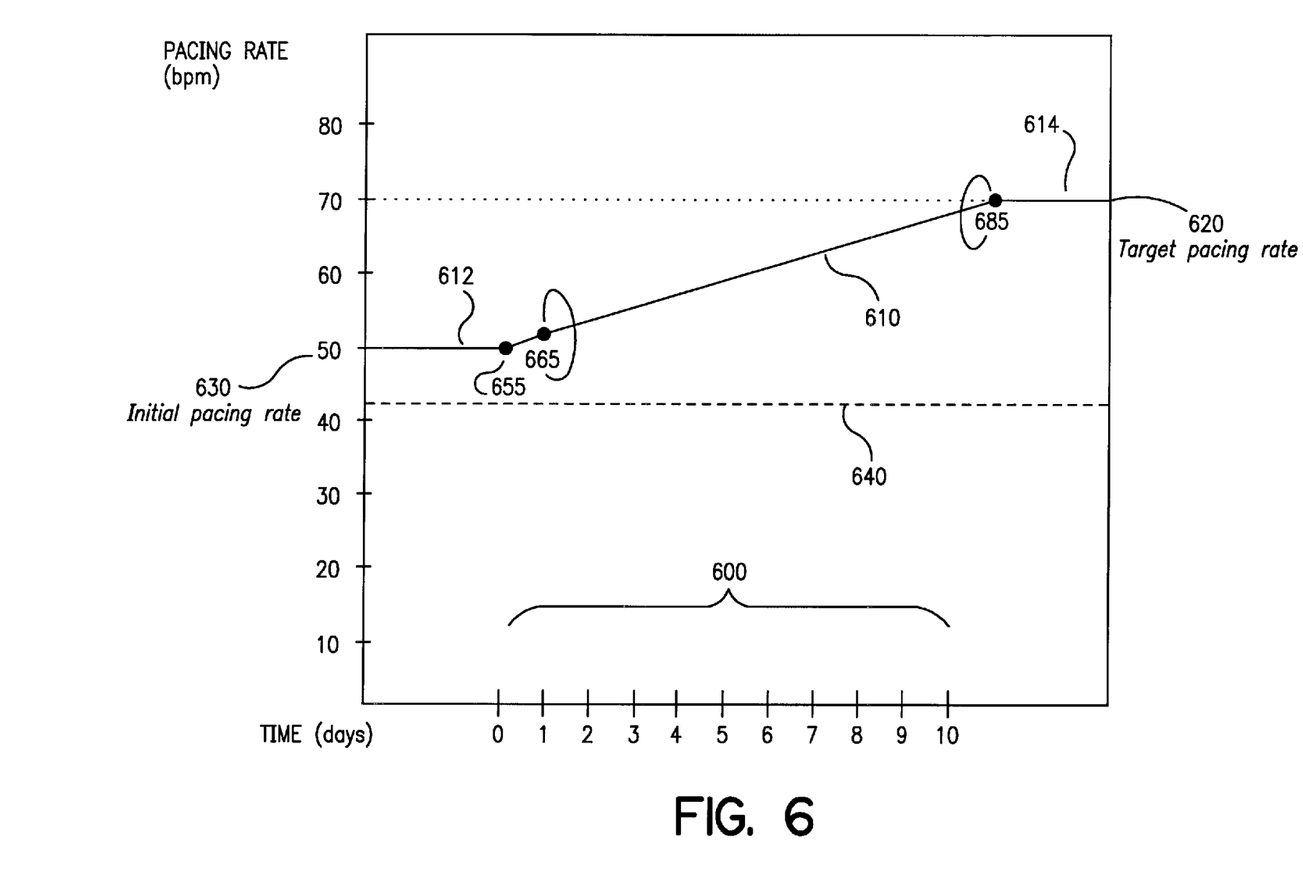
FIG. 6 illustrates a flow chart of a routine of a method of increasing a pace of a mammalian heart by an implantable medical device.

FIG. 6 illustrates one embodiment of a routine for a method and system for increasing a pacer function of IMD 10 disposed within mammalian heart 8. The method for increasing the pacer function of IMD 10 may be preferably performed by means of a computer algorithm program, which may be stored integral with, or remote from, IMD 10. Alternatively, the method described herein may be performed in any other similar manner.

The computer algorithm program may preferably be any program capable of being stored on an electronic medium, such as, for example, RAM 68 or ROM 70, and permitted to be accessed (and consequently run) by microprocessor 64. Alternatively, the method may be performed manually by a programmer electronically programming instructions to IMD 10, either remotely from a location away from IMD 10, or via an electronic connection with IMD 10.

In Block 100, computer algorithm software operating on microprocessor 64 of IMD 10 paces heart 8 according to a first pacing parameter. As mentioned above with regards to FIGS. 3 and 5, the pacing of heart 8 by IMD 10 occurs through the process of transmitting a first set of stimulus pulses to heart 8 from electrodes 2, 3, 9, 13. Electrodes 2, 3, 9, 13, in turn, receive pacing signals from pacer timing/control circuitry 63 through atrial pacer output circuitry 65 and ventricular pacer output circuitry 67. The first pacing parameter is preferably any pacer function capable of pacing heart 8 at the current physician-determined rate, capable of maintaining the current state of physical health of the patient. In this embodiment, the first pacing parameter is preferably a low heart rate, set at, for example, 50 beats per minute (bpm). Alternatively, the first pacing parameter may be any other rate responsive parameter able to pace heart 8 at the current physician-determined rate.

In Block 200, IMD 10 receives a command to increase the first pacing parameter. The increase command may be a signal instructing computer algorithm software operating on microprocessor 64 of IMD 10 to increase the pacing rate of heart 8. Alternatively, the increase command may be any other instruction or command signal indicating an increase of a rate responsive parameter of heart 8. The increase command may be transmitted to IMD 10 remotely, for example, from a programmer, through any known means of transmitting information to IMD 10. Alternatively, the increase command may be automatically initiated by controller 74 after the reception of an instruction from microprocessor 64 upon the occurrence of a specified event necessitating an increase in the first pacing parameter, such as, for example, when the generally increasing health of the patient necessitates an increase in the heart rate, the beginning of a patient's therapeutic program, or any other situation necessitating an increase in any rate responsive parameter of heart 8. Such a specified event may be stored in a memory location (i.e., on-board RAM 68 or ROM 70) within microprocessor 64 of IMD 10.

After receiving the increase command, in Block 300, IMD 10 may then receive a second pacing parameter. This second pacing parameter corresponds to an upper pacing limit or boundary of the first pacing parameter. In the example illustrated above, heart 8 is being paced at a first pacing parameter of 50 bpm. The second pacing parameter may instruct the computer algorithm software operating on microprocessor 64 of IMD 10 to increase the pacing rate of the heart to a higher pacing rate, such as, for example, 60 bpm. Similar to the case with the first pacing parameter, the pacing of heart 8 by IMD 10 at the second pacing parameter occurs through the process of transmitting a second set of stimulus pulses to heart 8 from electrodes 2, 3, 9, 13. Electrodes 2, 3, 9, 13, in turn, receive the pacing signals from pacer timing/control circuitry 63 through atrial pacer output circuitry 65 and ventricular pacer output circuitry 67.

Also, similar to the increase command, the reception of the second pacing parameter by IMD 10 may be transmitted to IMD 10 remotely, such as, from a programmer, through any known means of transmitting information to IMD 10. Alternatively, the increase of the first pacing parameter to the second pacing parameter may be automatically initiated by controller 74 by an instruction from microprocessor 64 upon the occurrence of a specified event necessitating an increase in a pacing parameter of heart 8, as specified above with regards to Block 200. Alternatively, the second pacing parameter may be pre-programmed into microprocessor 64, and then automatically set as the upper pacing limit upon receipt of the increase command (as illustrated in Block 200).

Next, in Block 400, IMD 10 receives a time interval. The time interval preferably corresponds to the time in which IMD 10 must increase the first pacing parameter to arrive at the second pacing parameter. For example, in the example provided, the time interval may require that IMD 10 increase the pacing rate of heart 8 from 50 bpm to 60 bpm within a span of ten days.

Similar to both the increase command and the second pacing parameter, the reception of the time interval by IMD 10 may be may be transmitted to IMD 10 remotely, such as, from a programmer, through any known means of transmitting information to IMD 10. Alternatively, the instructions contained within the time interval may be automatically determined and sent by microprocessor 64 to controller 74 upon the determination or reception of the second pacing parameter. That is, the time interval may be preset by IMD 10.

Next, in Block 500, IMD 10 receives an increment factor. The increment factor preferably corresponds to the increment with which computer algorithm software located on IMD 10 increases the first pacing parameter to the second pacing parameter. For example, in the example described above, the increment factor may require that computer algorithm software located on IMD 10 increase the first pacing parameter of heart 8 to 60 bpm by 1 bpm per day, until the second pacing parameter has been reached. The increment factor may either be a specified rate, such as, 1 bpm per day, or it may be a function of the time interval. For example, if the time interval is ten days, the increment proportion may be 10 percent per day.

The increment factor may also indicate the type of increase of the first pacing parameter of heart 8. For example, the increment factor may instruct the computer algorithm software located on microprocessor 64 of IMD 10 to increase the first pacing parameter to the second pacing parameter linearly. Alternatively, the increment factor may provide for a linear increase and/or decrease of the pacing interval (i.e., the time between successive increases of the first pacing parameter); a constant percentage change; a variable percentage change; an exponential change; etc.

Similar to the above parameters, the reception of the increment factor by IMD 10 may be may be transmitted to IMD 10 remotely, such as, from a programmer, through any known means of transmitting information to IMD 10. Alternatively, the instructions contained within the increment factor may be automatically determined and sent by microprocessor 64 to controller 74 upon the determination or reception of the second pacing parameter. That is, the increment factor may be preset by IMD 10.

Finally, in Block 600, computer algorithm software located on microprocessor 64 of IMD 10 increases the first pacing parameter to the second pacing parameter in accordance with the instructions received from Blocks 200, 300, 400 and 500. Thus, in the example illustrated above, computer algorithm software located on microprocessor 64 of IMD 10 increases the first pacing parameter of 50 bpm to 60 bpm by a factor of 1 bpm per day for a total period of ten days.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for increasing a pacing parameter of a mammalian heart. The present invention is also not limited to the increase of pacing parameters, per se, but may find further application as a measuring means. The present invention further includes within its scope methods of making and using the measurement means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

I claim:

1. A method of increasing a pacer function of an implantable medical device disposed within a mammalian heart, comprising:

pacing the mammalian heart according to a first pacing parameter;

receiving a command to increase the first pacing parameter;

receiving a second pacing parameter;

receiving a time interval; and increasing the first pacing parameter of the mammalian heart to the second pacing parameter during the time interval.

2. The method of claim 1, further comprising receiving an increment factor.

3. The method of claim 2, further comprising increasing the first pacing parameter of the mammalian heart to the second pacing parameter during the time interval by the increment factor.

4. The method of claim 1, wherein the command is preprogrammed into the implantable medical device.

5. The method of claim 1, wherein the first pacing parameter is a heart beat.

6. The method of claim 1, wherein the second pacing parameter is a heart beat.

7. The method of claim 1, wherein the first pacing parameter is a rate response parameter.

8. The method of claim 1, wherein the first pacing parameter is a rate response parameter.

9. The method of claim 1, wherein the second pacing parameter is preprogrammed into the implantable medical device.

10. The method of claim 1, wherein the time interval is preprogrammed into the implantable medical device.

11. The method of claim 2, wherein the increment factor is preprogrammed into the implantable medical device.

12. The method of claim 11, wherein the preprogrammed increment factor is a function of the time interval.

13. An implantable medical device comprising:

a processor;

a controller operably connected to the processor; and at least one pacing lead operably connected to the controller; wherein a first pacing parameter of a mammalian heart is increased to a second pacing parameter in accordance with a time interval when a signal is sent to one of the at least one pacing leads from the controller upon reception by the processor of a command to increase the first pacing parameter by the processor.

14. The implantable medical device of claim 13, wherein the processor further receives an increment factor.

15. The implantable medical device of claim 14, further comprising increasing the first pacing parameter to the second pacing parameter during the time interval by the increment factor.

16. The implantable medical device of claim 13, wherein the command is preprogrammed into the implantable medical device.

17. The implantable medical device of claim 13, wherein the first pacing parameter is a heart beat.

18. The implantable medical device of claim 13, wherein the second pacing parameter is a heart beat.

19. The implantable medical device of claim 13, wherein the first pacing parameter is a rate response parameter.

20. The implantable medical device of claim 13, wherein the second pacing parameter is a rate response parameter.

21. The implantable medical device of claim 13, wherein the second pacing parameter is preprogrammed into the implantable medical device.

22. The implantable medical device of claim 13, wherein the time interval is preprogrammed into the implantable medical device.

23. The implantable medical device of claim 14, wherein the increment factor is preprogrammed into the implantable medical device.

24. The implantable medical device of claim 23, wherein the preprogrammed increment factor is a function of the time interval.

25. An implantable medical device system for increasing a pacer function of an implantable medical device disposed within a mammalian heart, comprising:

means for pacing the mammalian heart according to a first pacing parameter;

means for receiving a command to increase the first pacing parameter;

means for receiving a second pacing parameter;

means for receiving a time interval; and means for increasing the first pacing parameter of the mammalian heart to the second pacing parameter during the time interval.

26. The implantable medical device system of claim 25, further comprising means for receiving an increment factor.

27. The implantable medical device system of claim 26, further comprising means for increasing the first pacing parameter of the mammalian heart to the second pacing parameter during the time interval by the increment factor.

28. The implantable medical device system of claim 25, wherein the command is preprogrammed into the implantable medical device.

29. The implantable medical device system of claim 25, wherein the first pacing parameter is a heart beat.

30. The implantable medical device system of claim 25, wherein the second pacing parameter is a heart beat.

31. The implantable medical device system of claim 25, wherein the first pacing parameter is a rate response parameter.

32. The implantable medical device system of claim 25, wherein the second pacing parameter is a rate response parameter.

33. The implantable medical device system of claim 25, wherein the second pacing parameter is preprogrammed into the implantable medical device.

34. The implantable medical device system of claim 25, wherein the time interval is preprogrammed into the implantable medical device.

35. The implantable medical device system of claim 26, wherein the increment factor is preprogrammed into the implantable medical device.

36. The implantable medical device system of claim 35, wherein the preprogrammed increment factor is a function of the time interval.

37. A computer usable medium for storing a program for increasing a pacer function of an implantable medical device disposed within a mammalian heart, comprising:

computer readable program code that paces the mammalian heart according to a first pacing parameter;

computer readable program code that receives a command to increase the first pacing parameter;

computer readable program code that receives a second pacing parameter;

computer readable program code that receives a time interval; and computer readable program code that increases the first pacing parameter of the mammalian heart to the second pacing parameter during the time interval.

38. The program of claim 37, further comprising computer readable program code that receives an increment factor.

39. The program of claim 38, further comprising computer readable program code that increases the first pacing parameter of the mammalian heart to the second pacing parameter during the time interval by the increment factor.

40. The program of claim 37, wherein the command is preprogrammed into the implantable medical device.

41. The program of claim 37, wherein the first pacing parameter is a heart beat.

42. The program of claim 37, wherein the second pacing parameter is heart beat.

43. The program of claim 37, wherein the first pacing parameter is a rate response parameter.

44. The program of claim 37, wherein the second pacing parameter is a rate response parameter.

45. The program of claim 37, wherein the second pacing parameter is preprogrammed into the implantable medical device.

46. The program of claim 37, wherein the time interval is preprogrammed into the implantable medical device.

47. The program of claim 38, wherein the increment factor is preprogrammed into the implantable medical device.

48. The program of claim 47, wherein the preprogrammed increment factor is a function of the time interval.

* * * * *